United States Patent [19]

D'Amico

[11] 4,185,990
[45] Jan. 29, 1980

[54] IMIDES DERIVED FROM 2-OXO-3-BENZOTHIAZOLINEACETIC ACID AND BUTYRIC ACID

[75] Inventor: John J. D'Amico, Olivette, Mo.

[73] Assignee: Monsanto Company, St. Louis, Mo.

[21] Appl. No.: 937,231

[22] Filed: Aug. 28, 1978

[51] Int. Cl.$^2$ .................. A01N 9/12; A01N 9/22; C07D 277/68

[52] U.S. Cl. .................... 71/90; 548/170; 548/171

[58] Field of Search .............. 260/304 B, 304 D; 71/90

[56] References Cited

U.S. PATENT DOCUMENTS

| | | | |
|---|---|---|---|
| 4,049,419 | 9/1977 | D'Amico | 71/90 |
| 4,075,216 | 2/1978 | D'Amico | 71/90 |
| 4,086,241 | 4/1978 | Wu et al. | 71/90 |

OTHER PUBLICATIONS

Davidson et al., "Journ. Amer. Chem. Soc.," vol. 80, 1958, pp. 376–379.
Polya et al., "Journ. Chem. Soc.," London, 1948, pp. 1081–1083.
Challis et al., "Chemistry of Cyan Groups", pp. 766–767.

*Primary Examiner*—Glennon H. Hollrah
*Assistant Examiner*—James H. Turnipseed
*Attorney, Agent, or Firm*—Richard H. Shear; Donald W. Peterson

[57] ABSTRACT

Imides derived from 2-oxo-3-benzothiazolineacetic acid and butyric acid have been found to be effective as herbicides and plant growth regulators.

22 Claims, No Drawings

Control of undesirable weed growth may be obtained by applying the herbicidal active ingredient to the plant locus which is defined herein to include the growth medium surrounding the plant, the seeds, emerging seedlings, roots, stems, leaves, flowers and other plant parts. Application to the leaves or stems after the weed has emerged from the soil is preferred. This type of treatment is known to those skilled in the art as a post-emergent treatment.

To illustrate the herbicidal properties of the compounds of the present invention, said compounds were tested in the following manner.

The pre-emergent test was conducted as follows:

A good grade of top soil was placed in aluminum pans and compacted to a depth of 0.95 to 1.27 cm. from the top of the pan. On the top of the soil was placed a predetermined number of seeds or vegetative propagules of various plant species which are compacted to soil level. The soil required to level fill the pans after seeding or adding vegetative propagules was weighed into a pan. A known amount of the herbicidal active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

As noted in Tables III and IV, below, approximately 2 or 4 weeks after seeding and treating, the plants were observed to determine all deviations from the normal growth habit and the results recorded. A herbicidal rating code was used to signify the extent of phytotoxicity of each species. The ratings are defined as follows:

| % Control | Rating |
|---|---|
| 0–24 | 0 |
| 25–49 | 1 |
| 50–74 | 2 |
| 75–100 | 3 |

The plant species utilized in these tests are identified by letter in accordance with the following legend:

| | |
|---|---|
| A - Canada Thistle | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge | Q - Wild Buckwheat |
| H - Quackgrass | R - Hemp Sesbania |
| I - Johnsongrass | S - Panicum Spp |
| J - Downy Brome | T - Crabgrass |

Results of the pre-emergent tests are summarized in Tables III and IV, below.

Table III

| Compound of Example No. | WAT* | kg h | A | B | C | D | E | F | G | H | I | J | K |
|---|---|---|---|---|---|---|---|---|---|---|---|---|---|
| 5 | 4 | 5.6 | 3 | 3 | 3 | 2 | 2 | 2 | 0 | 1 | 0 | 0 | 0 |
| 6 | 4 | 5.6 | 2 | 2 | 1 | 3 | 3 | 1 | 0 | 3 | 0 | 2 | 0 |
| 7 | 4 | 5.6 | 3 | 2 | 2 | 2 | 3 | 1 | 0 | 0 | 0 | 0 | 0 |
| 8 | 2 | 5.6 | 0 | 0 | 0 | 0 | 1 | 0 | 0 | 0 | 0 | 0 | 0 |
| 9 | 4 | 5.6 | 3 | 2 | 2 | 1 | 1 | 2 | 0 | 3 | 3 | 0 | 0 |
| 10 | 4 | 11.2 | 3 | 2 | 2 | 2 | 3 | 2 | — | 1 | 1 | 0 | 0 |
| 11 | 4 | 11.2 | 0 | 0 | 0 | 0 | 0 | 0 | 0 | 0 | 0 | 0 | 0 |

*Weeks after treatment.

Table IV

| Compound of Example No. | WAT* | kg h | L | M | N | O | P | B | Q | D | R | E | F | C | J | S | K | T |
|---|---|---|---|---|---|---|---|---|---|---|---|---|---|---|---|---|---|---|
| 5 | 3 | 5.6 | 3 | 3 | 2 | 1 | 1 | 3 | 3 | 2 | 3 | 3 | 3 | 3 | 0 | 1 | 1 | 1 |
| 5 | 3 | 1.12 | 2 | 1 | 0 | 0 | 0 | 3 | 3 | 2 | 3 | 2 | 2 | 2 | 0 | 1 | 1 | 2 |
| 5 | 2 | 0.28 | 0 | 0 | 0 | 0 | 0 | 0 | 0 | 0 | 0 | 0 | 0 | 0 | 0 | 0 | 0 | 0 |
| 5 | 2 | 0.056 | 0 | 0 | 0 | 0 | 0 | 0 | 0 | 0 | 0 | 0 | 0 | 0 | 0 | 0 | 0 | 0 |
| 6 | 2 | 1.12 | 0 | 0 | 0 | 0 | 0 | 0 | 0 | 0 | — | 0 | 0 | 0 | 1 | 0 | 3 | |
| 6 | 2 | 0.28 | 0 | 0 | 0 | 0 | 0 | 0 | 0 | 0 | — | 0 | 0 | 0 | 0 | 0 | 2 | |
| 6 | 2 | 0.056 | 0 | 0 | 0 | 0 | 0 | 0 | 0 | 0 | — | 0 | 0 | 0 | 0 | 0 | — | |

*Weeks after treatment.

The post-emergent tests were conducted as follows:

The herbicidal active ingredients are applied in spray form to two or three-week old specimens of various plant species. The spray, a solution or wettable powder suspension containing the appropriate rate of herbicidal active ingredient to give the desired test rate and a surfactant, is applied to the plants. The treated plants are placed in a greenhouse and approximately two or four weeks later the effects are observed and recorded. The results are shown in Tables V and VI in which the post-emergent herbicidal rating code is as follows:

| % Control | Rating |
|---|---|
| 0–24 | 0 |
| 25–49 | 1 |
| 50–74 | 2 |
| 75–99 | 3 |
| 100 | 4 |

The plant species utilized in these tests are identified by letter in accordance with the previous legend.

Table V

| Compound of Example No. | WAT* | kg h | A | B | C | D | E | F | G | H | I | H | K |
| --- | --- | --- | --- | --- | --- | --- | --- | --- | --- | --- | --- | --- | --- |
| 5 | 4 | 5.6 | 2 | 2 | 2 | 1 | 3 | 1 | 0 | 0 | 0 | 0 | 0 |
| 6 | 2 | 5.6 | 1 | 1 | 1 | 1 | 3 | 0 | 0 | 0 | 0 | 0 | 0 |
| 7 | 4 | 5.6 | 2 | 2 | 1 | 2 | 3 | 1 | 0 | 0 | 0 | 0 | 2 |
| 8 | 2 | 5.6 | 0 | 0 | 0 | 0 | 0 | 0 | 0 | 0 | 0 | 0 | 0 |
| 9 | 4 | 5.6 | 1 | 2 | 2 | 2 | 2 | 2 | 0 | 0 | 0 | 0 | 0 |
| 10 | 4 | 11.2 | 3 | 2 | 2 | 2 | 3 | 2 | 0 | 0 | 0 | 0 | 1 |
| 11 | 4 | 11.2 | 0 | 0 | 0 | 0 | 3 | 0 | 0 | 0 | 0 | 0 | 0 |

*Weeks after treatment.

Table VI

| Compound of Example No. | WAT* | kg h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| 7 | 2 | 1.12 | 1 | 1 | 0 | 0 | 0 | 2 | 1 | 1 | 0 | 1 | 0 | 2 | 0 | 0 | 0 | 0 |
| 7 | 2 | 0.28 | 1 | 0 | 0 | 0 | 0 | 1 | 1 | 1 | 0 | 2 | 0 | 1 | 0 | 0 | 0 | 0 |

*Weeks after treatment.

The above tables illustrate one aspect of the present invention, that is, the use of the compounds of the invention to kill or injure undesirable plants, e.g., weeds. Another aspect of the invention, however, is the use of the imides of formula (I) for the regulation of desirable plant growth, especially leguminous plants such as soybeans. More particularly, it has been found that compounds of the foregoing formula (I), with the exception of those wherein T is bromo, have been found to be effective in regulating the growth of leguminous plants.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth when used as a plant growth regulant, it does not include the total inhibition or killing of such plants. The present invention contemplates the use of an amount of the imide of formula (I) as the active ingredient in a plant growth regulating composition which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to the plant locus which has been defined herein to include the growth medium surrounding the plant, the seeds, emerging seedlings, roots, stems, leaves, flowers, or other plant parts. Such application may be made directly to the plant part, or indirectly by application to the plant growth medium.

Utilizing the imide of formula (I) as the active ingredient in a plant growth regulating composition, said compounds were found to possess plant growth regulating activity when tested in accordance with the following procedure.

A number of soybean plants, variety Williams, were grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 was used as a surfactant.

When the fifth trifoliate leaf (four to five weeks) was fully expanded, the treated plants were compared with the non-treated control plants and the observations recorded. Those observations are summarized in Table VII, below.

Table VII

| Compound of Example No. | Rate (kg/h) | Observations |
| --- | --- | --- |
| 5 | 2.8 | Stature reduction, inhibition of dry weight, stem distortion, leaf alteration, leaf inhibition, altered canopy, slight leaf burn. |
| 5 | 0.56 | Inhibition of dry weight, leaf alteration of old and new growth, leaf inhibition, altered canopy. |
| 5 | 0.112 | Leaf alteration of old and new growth. |
| 9 | 2.8 | Stature reduction, inhibition of dry weight, stem distortion, leaf inhibition, leaf distortion of new growth. |
| 9 | 0.56 | Stature reduction, inhibition of dry weight, leaf inhibition, leaf distortion of new growth. |
| 9 | 0.112 | Leaf inhibition, leaf distortion of new growth. |
| 10 | 2.8 | Stature reduction, inhibition of dry weight, epinasty, leaf distortion of old and new growth, leaf inhibition, moderate leaf burn. |
| 10 | 0.56 | Stature reduction, inhibition of dry weight, stem distortion, leaf dis- |

IMIDES DERIVED FROM 2-OXO-3-BENZOTHIAZOLINEACETIC ACID AND BUTYRIC ACID

This invention relates to imides derived from amides of 2-oxo-3-benzothiazolineacetic acid and butyric acid. The compounds have been found to be effective agricultural chemicals useful as herbicides as well as plant growth regulants.

The compounds may be represented by the formula

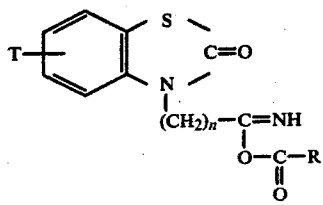

wherein R is lower alkyl, T is hydrogen, halogen, nitro or lower alkyl, and n is either one or three.

The term "lower alkyl" as used herein is understood to include those alkyl groups having up to five carbon atoms, inclusive. Both straight as well as branched chain alkyl groups are contemplated.

The term "halogen" as used herein includes chloro, bromo, fluoro and iodo.

Unexpectedly, it has been found that a catalyst consisting of the alkali metal salt of a lower alkanoic acid having the formula

must be utilized. In the above formula, M represents an alkali metal.

The amide precursor may be prepared in accordance with U.S. Pat. No. 4,049,419 by reacting the appropriate substituted 2-benzothiazolinone with potassium hydroxide and an amide of chloroacetic acid or chlorobutyric acid. The following examples are illustrative of this procedure and are presented merely to illustrate the above procedure wherein Compounds 1-3 of Table I may be prepared as follows and are not intended as a limitation on the scope of the invention.

To a stirred solution containing 0.2 mole of the appropriate 5- or 6-substituted 2-benzothiazolinone, 13.2 g (0.2 mole) of 85% potassium hydroxide in 250 ml. of acetone containing 20 ml. of water, 0.2 mole of 2-chloroacetamide is added in one portion. The stirred reaction mixture is heated at reflux for 6 hours and then at 25°-30° C. for 18 hours. After the addition of 700 ml. of water, stirring is continued at 25°-30° C. for 30 minutes. The solid is collected by filtration, washed with water until neutral and air-dried at 25°-30° C. The data are summarized in Table I.

Table I

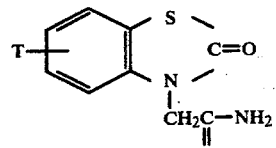

| Compound of Example No. | T | M.P. °C. | % Yield | Percent C Calc'd. | Percent C Found | Percent H Calc'd. | Percent H Found | N Calc'd. | N Found | Percent S Calc'd. | Percent S Found |
|---|---|---|---|---|---|---|---|---|---|---|---|
| 1 | 6-Br | 278-9 | 80 | 37.65 | 37.77 | 2.46 | 2.51 | 9.76 | 9.80 | 11.17 | 11.27 |
| 2 | 5-Cl | 284-5[a] | 84 | 44.54 | 44.62 | 2.91 | 2.90 | 11.54 | 11.58 | 13.21 | 13.13 |
| 3 | 6-NO$_2$ | 297-8[a] | 54 | 42.69 | 42.62 | 2.79 | 2.79 | 16.59 | 16.57 | 12.66 | 12.66 |

[a]Recrystallization from DMF.

The imides of the foregoing formula are prepared by the appropriate amide with an anhydride in accordance with the following reaction scheme:

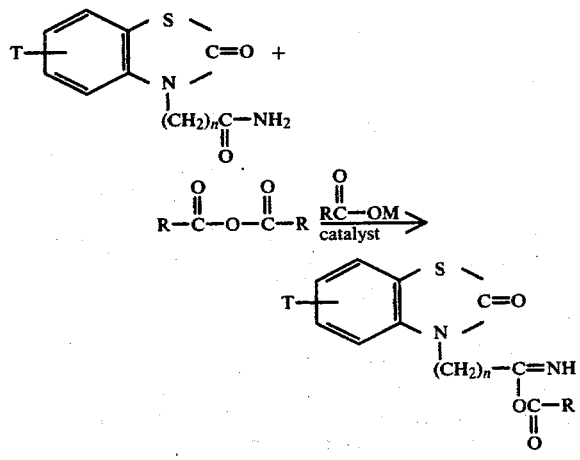

The amide precursor may also be prepared by reaction of the appropriate nitrile with concentrated sulfuric acid.

EXAMPLE 4

To 75 ml. of concentrated sulfuric acid at −20° C., 43.7 g (0.2 mole) of 2-oxo-3-benzothiazolinebutyronitrile is added in small portions at −20° to 0° C. Cooling is removed and stirring is continued at 25°-30° C. for 2 days. After cooling to −10° C., 800 g of ice water is added in small portions while maintaining the temperature below 25° C. After cooling to 0° C., 250 ml. of concentrated ammonium hydroxide is added dropwise at 0° to 25° C. The reaction mixture is stirred at 25°-30° C. for 30 minutes, the solid is collected by filtration, washed with water until neutral and air-dried at 25°-30° C. The product which is 2-oxo-3-benzothiazolinebutyric acid amide, m.p. 145°-6° C., is obtained in 80% yield.

Anal. Calc'd. for $C_{11}H_{12}N_2O_2S$: C, 55.91; H, 5.12; N, 11.86; S, 13.57. Found: C, 55.94; H, 5.15; N, 11.85; S, 13.51.

As noted above, the imides of the invention are prepared by reaction of the appropriate amide with an anhydride. Examples 5-11 are presented below to illustrate said process.

EXAMPLE 5

A stirred slurry containing 0.1 moles of 2-oxo-3-benzothiazolineacetamide, 150 ml. of acetic anhydride and 2 g of sodium acetate is heated at reflux (138°-140° C.) for two hours to form a solution. After cooling the stirred solution to 5° C., 800 g of ice water is added and stirring continued at 0-10° C. for 1 to 2 hours. The solid having the formula

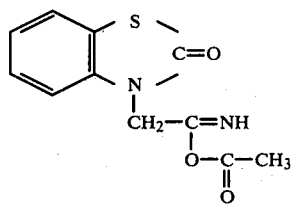

is collected by filtration, washed with water until neutral to litmus and air-dried at 25°-30° C. Recrystallization from isopropyl alcohol resulted in a product having a melting point of 148° C. The yield obtained was 74%. Anal. Calc'd: C, 52.79; H, 4.03; N, 11.19; S, 12.81. Found: C, 52.94; H, 4.05; N, 11.30; S, 12.63.

EXAMPLE 6

The procedure of Example 5 is repeated utilizing 6-bromo-2-oxo-3-benzothiazolineacetamide in lieu of 2-oxo-3-benzothiazolineacetamide. In addition, 200 ml. of the anhydride was utilized in lieu of 150 ml. Data is summarized in Table II.

EXAMPLE 7

The procedure of Example 6 is repeated utilizing 5-chloro-2-oxo-3-benzothiazolineacetamide in lieu of 6-bromo-2-oxo-3-benzothiazolineacetamide. Data is summarized in Table II.

EXAMPLE 8

The procedure of Example 6 is repeated utilizing 6-nitro-2-oxo-3-benzothiazolineacetamide in lieu of 6-bromo-2-oxo-3-benzothiazolineacetamide. Data is summarized in Table II.

EXAMPLE 9

The procedure of Example 5 is repeated utilizing propionic anhydride and 2 g of sodium propionate in lieu of acetic anhydride and sodium acetate. Data is summarized in Table II.

EXAMPLE 10

The procedure of Example 5 is repeated utilizing butyric anhydride and 2 g of sodium butyrate in lieu of acetic anhydride and sodium acetate. Data is summarized in Table II.

EXAMPLE 11

The procedure of Example 5 is repeated utilizing 2-oxo-3-benzothiazolinebutyramide in lieu of 2-oxo-3-benzothiazolineacetamide. Data is summarized in Table II.

Table II

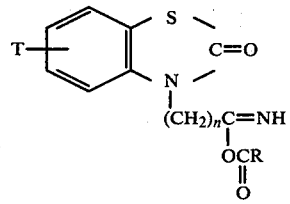

| Compound of Example No. | T | n | R | m.p. °C. | % Yield | | % C | % H | % N | % S |
|---|---|---|---|---|---|---|---|---|---|---|
| 6 | 6-Br | 1 | —CH$_3$ | 216-8$^{(a)}$ | 91 | Calc'd: | 40.14 | 2.76 | 8.51 | 9.74 |
| | | | | | | Found: | 40.14 | 2.76 | 8.49 | 9.76 |
| 7 | 5-Cl | 1 | —CH$_3$ | 209-11$^{(a)}$ | 82 | Calc'd: | 46.40 | 3.19 | 9.84 | 11.26 |
| | | | | | | Found: | 46.43 | 3.19 | 9.82 | 11.20 |
| 8 | 6-NO$_2$ | 1 | —CH$_3$ | 227-8$^{(b)}$ | 86 | Calc'd: | 44.59 | 3.40 | 14.18 | 10.82 |
| | | | | | | Found: | 44.68 | 3.09 | 14.25 | 10.87 |
| 9 | H | 1 | —C$_2$H$_5$ | 188-9$^{(a)}$ | 60 | Calc'd: | 54.53 | 4.58 | 10.60 | 12.13 |
| | | | | | | Found: | 54.55 | 4.58 | 10.73 | 12.10 |
| 10 | H | 1 | —C$_3$H$_7$ | 152-3 | 57 | Calc'd: | 56.10 | 5.07 | 10.06 | 11.52 |
| | | | | | | Found: | 56.14 | 5.09 | 10.07 | 11.50 |
| 11 | H | 3 | —CH$_3$ | 132-4$^{(c)}$ | 22 | Calc'd: | 56.10 | 5.07 | 10.06 | 11.52 |
| | | | | | | Found: | 56.09 | 5.07 | 10.08 | 11.53 |

$^{(a)}$Recrystallization from isopropyl alcohol.
$^{(b)}$Recrystallization from ethyl acetate.
$^{(c)}$Recrystallization from methyl alcohol.

One aspect of the present invention is the discovery that the reaction of the amide with the appropriate anhydride requires the use of a catalyst comprising an alkali metal salt of the acid corresponding to the anhydride. If a catalyst is not used, the product obtained is a mixture comprising three components, an imide, a nitrile and an unknown. Use of the catalyst, especially the sodium salt of the acid corresponding to the anhydride, significantly reduces the formation of the nitrile and the unknown resulting in a relatively pure product consisting of the desired imide.

In accordance with the second aspect of the present invention, the imides of the foregoing formula (I) have been found to be effective as herbicides. The compounds may be used by themselves or as the active ingredient in a herbicidal composition.

As used herein, the term "herbicidal active ingredient" is understood to mean an imide of the foregoing formula (I).

Table VII-continued

| Compound of Example No. | Rate (kg/h) | Observations |
|---|---|---|
| | | tortion of old and new growth, leaf inhibition, slight leaf burn. |
| 10 | 0.112 | Inhibition of dry weight, leaf distortion, leaf alteration of new growth, leaf inhibition, slight leaf burn. |
| 11 | 2.8 | Inhibition of dry weight, leaf inhibition, leaf alteration of new growth, slight leaf burn. |
| 11 | 0.56 | Leaf alteration of new growth. |
| 11 | 0.112 | Leaf alteration of new growth. |

As can be seen from the above data, the imide of formula (I) above is especially effective at rates of about 2.8 kilograms per hectare in reducing the stature of soybean plants. At lower rates, the compounds are effective in altering the leaf morphology of the plant without reducing the plant's stature.

Thus, the above data illustrate that the compounds of the invention may be used as a herbicide or a plant growth regulant. When used as a herbicide, it is desirable that rates of application about 1.12 kilograms per hectare and above be utilized. When used to regulate the growth of desirable plants, rates below 5.6 kilograms per hectare, especially 0.056 to 2.8, are preferred.

In selecting the appropriate time and rate of application of the active ingredient, it will be recognized that precise rates will also be dependent upon the desired response, mode of application, plant variety, soil conditions and various other factors known to those skilled in the art. In addition, it will be recognized that single or multiple applications may be used to exert the desired response.

In the practice of the invention, the active ingredient, whether used as a herbicide or a plant growth regulant, can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention, whether used as a herbicide or a plant growth regulant, generally contain from about 5 to 95 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

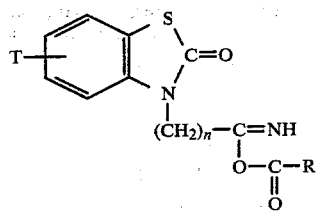

wherein R is lower alkyl, T is hydrogen, halogen, nitro or lower alkyl, and n is either one or three.

2. A compound according to claim 1 wherein n is one.
3. A compound according to claim 1 wherein T is hydrogen.
4. A compound according to claim 1 wherein R is methyl.
5. A compound according to claim 3 wherein R is methyl.
6. A method for preventing the growth of undesirable plants which comprises applying to the plant locus a herbicidally effective amount of a compound having the formula

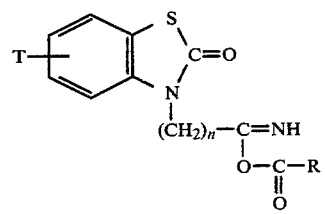

wherein R is lower alkyl, T is hydrogen, halogen, nitro or lower alkyl, and n is either one or three.

7. A method according to claim 6 wherein n is one.
8. A method according to claim 6 wherein T is hydrogen.
9. A method according to claim 6 wherein R is methyl.
10. A method according to claim 8 wherein R is methyl.

11. A method of regulating the growth of desirable leguminous plants which comprises applying to the plant locus a plant growth regulating effective amount of a compound having the formula

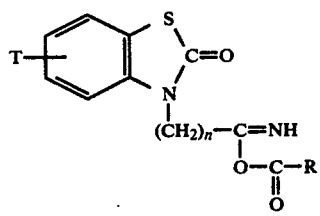

wherein R is lower alkyl, T is hydrogen, halogen, nitro or lower alkyl, and n is either one or three; with the proviso that T may not be bromo.

12. A method according to claim 11 wherein n is one.
13. A method according to claim 11 wherein T is hydrogen.
14. A method according to claim 11 wherein R is methyl.
15. A method according to claim 13 wherein R is methyl.
16. An agricultural chemical composition which comprises from about 5 to about 95 parts by weight of a compound having the formula

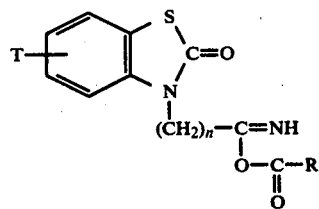

wherein R is lower alkyl, T is hydrogen, halogen, nitro or lower alkyl, and n is either one or three; the remaining parts being comprised of one or more suitable adjuvants, carriers and/or diluents.

17. A composition according to claim 16 wherein n is one.
18. A composition according to claim 16 wherein T is hydrogen.
19. A composition according to claim 16 wherein R is methyl.
20. A composition according to claim 18 wherein R is methyl.
21. A method for the preparation of a compound having the formula

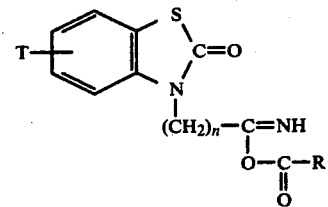

wherein R is lower alkyl, T is hydrogen, halogen, nitro or lower alkyl, and n is either one or three which comprises reacting

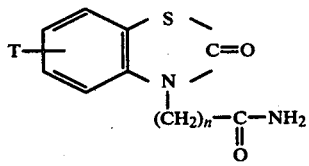

and

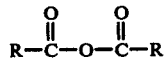

in the presence of a catalytic amount of a salt having the formula

wherein M is an alkali metal.

22. A method according to claim 21 wherein M is sodium.

* * * * *